United States Patent
Sonnabend et al.

(10) Patent No.: US 6,884,246 B1
(45) Date of Patent: Apr. 26, 2005

(54) BONE RESECTION DEVICE

(75) Inventors: David H. Sonnabend, Rose Bay (AU); William Graves, Cheltenham (AU); William R. Walsh, Macoubra (AU)

(73) Assignee: DePuy International Limited, Leeds (GB)

( * ) Notice: Subject to any disclaimer, the term of this patent is extended or adjusted under 35 U.S.C. 154(b) by 110 days.

(21) Appl. No.: 10/129,641

(22) PCT Filed: Nov. 10, 2000

(86) PCT No.: PCT/GB00/04301

§ 371 (c)(1),
(2), (4) Date: Oct. 8, 2002

(87) PCT Pub. No.: WO01/34040

PCT Pub. Date: May 17, 2001

(30) Foreign Application Priority Data

Nov. 10, 1999 (GB) .............................. 9926564

(51) Int. Cl.⁷ ............................................. A61B 17/00
(52) U.S. Cl. .............................. 606/80; 606/82; 606/84
(58) Field of Search ................ 606/86, 87, 79–81, 606/96, 97, 167, 170–172, 178, 180, 80, 82, 84, 177; 408/157, 158, 154, 147, 161

(56) References Cited

U.S. PATENT DOCUMENTS

| | | | | |
|---|---|---|---|---|
| 3,702,611 A | * | 11/1972 | Fishbein ...................... 606/81 |
| 4,992,010 A | * | 2/1991 | Fischer ........................ 408/159 |
| 5,509,918 A | * | 4/1996 | Romano ....................... 606/80 |
| 5,817,095 A | | 10/1998 | Smith | |
| 5,853,054 A | * | 12/1998 | McGarian et al. .......... 175/267 |
| 6,383,188 B1 | * | 5/2002 | Kuslich et al. ............... 606/80 |

FOREIGN PATENT DOCUMENTS

| | | |
|---|---|---|
| DE | 38 40 466 | 7/1990 |
| DE | 38 40 466 A1 | 7/1990 |
| EP | 05 33 320 | 3/1993 |
| EP | 0 661 023 A2 | 7/1995 |
| FR | 2 606 267 A1 | 11/1987 |
| WO | WO 94 09 730 | 11/1994 |

* cited by examiner

*Primary Examiner*—Pedro Philogene
(74) *Attorney, Agent, or Firm*—Maginot Moore & Beck

(57) ABSTRACT

A bone resection device (30) for use in resection of bone during joint replacement surgery includes a rotatable shaft (4) having mounted thereon for rotation with the shaft at least two blades (3) carrying at least one cutting edge (3a). The bone resection device (30) further includes a blade positioning mechanism (2) mounted on the device or engaging with the device at least during use thereof and arranged to cooperate with the blades during rotation thereof to alter the orientation of the cutting edge relative to the shaft such that the shape of the resected surface is determined at least in part by the blade positioning mechanism.

20 Claims, 5 Drawing Sheets

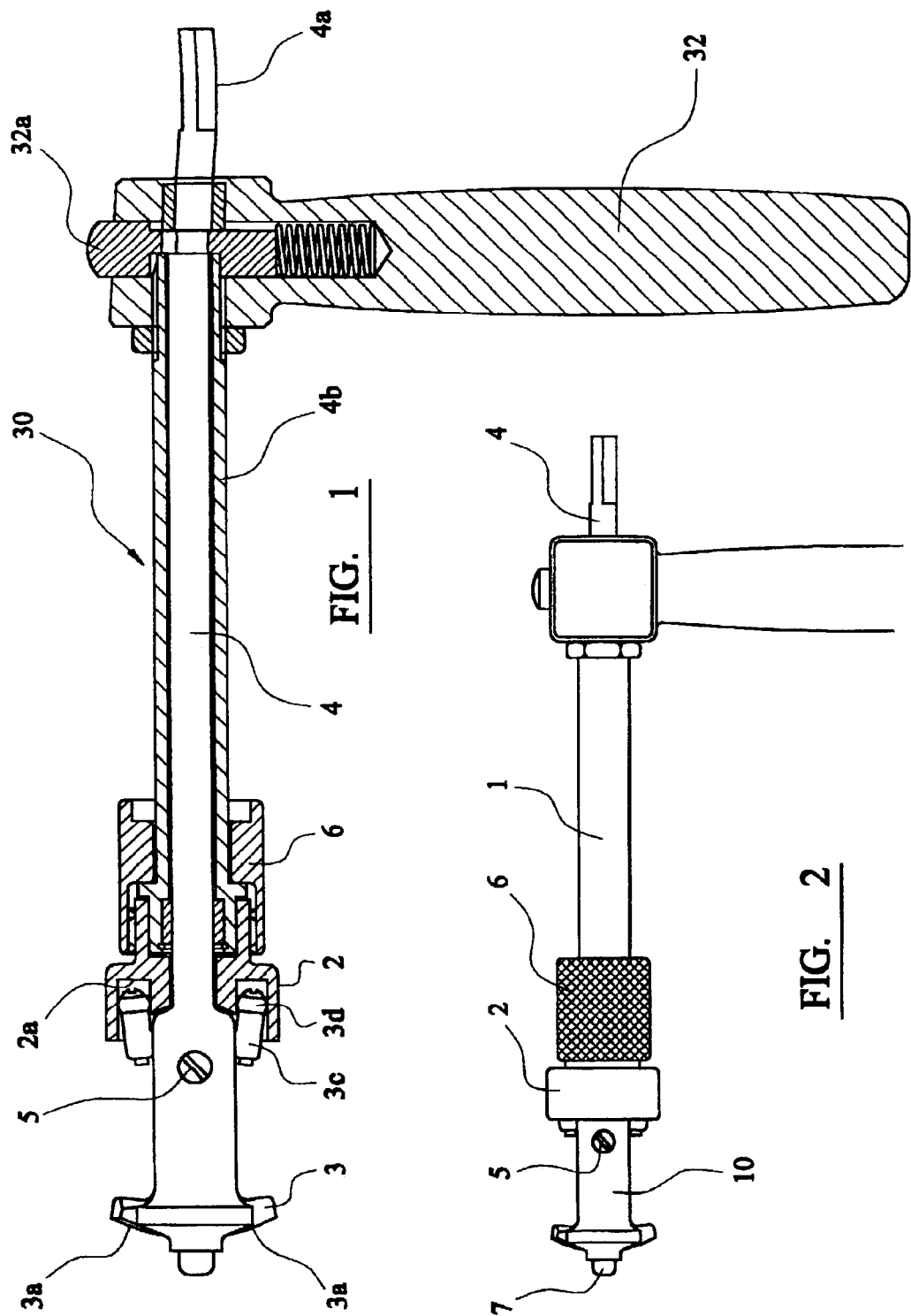

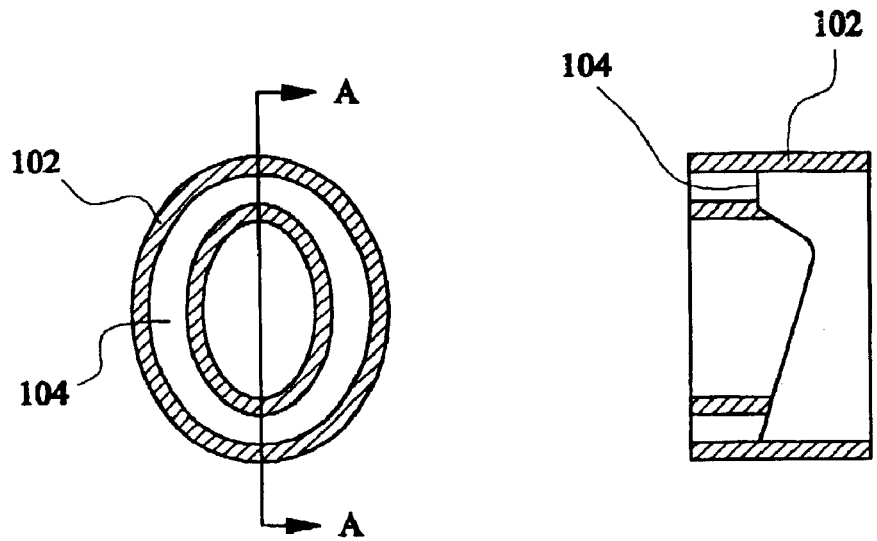
FIG. 9A  FIG. 9B
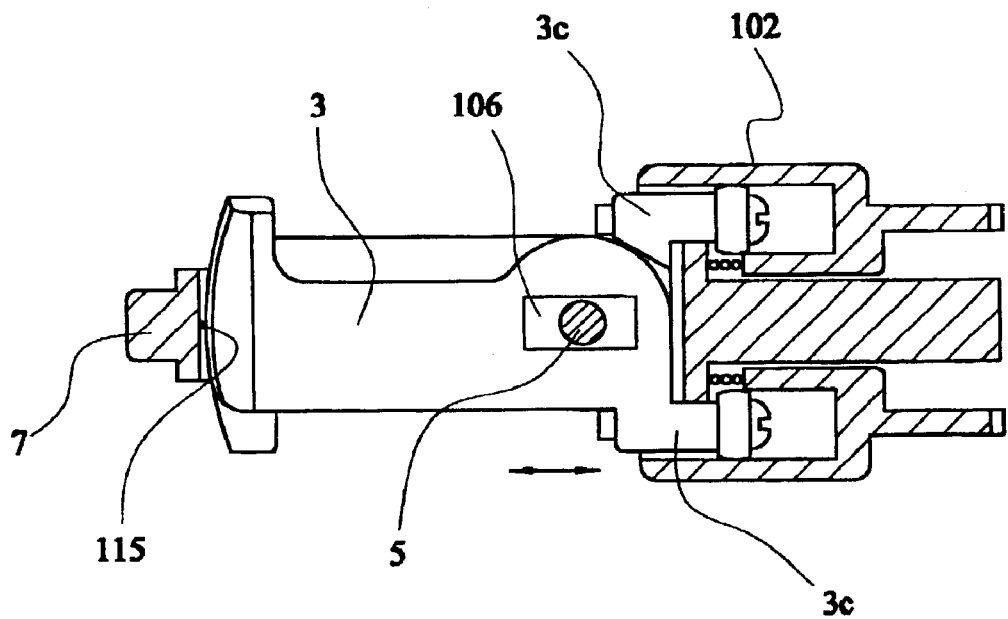
FIG. 10

BONE RESECTION DEVICE

The present invention relates to a surgical instrument for the controlled removal of bone during joint replacement surgery.

Such instruments are commonly referred to as reamers or millers. Conventionally available instruments generate a resected surface which is of fixed shape (for example circular), dependent upon the particular instrument used. However, sometimes it is necessary to cut more complex shapes, and attempts have been made to provide instrumentation capable of this.

WO-94/09730 discloses a cutting guide with cylindrically shaped openings whose respective central longitudinal axes form an acute angle. A surgeon can form two overlapping circular cuts, which together form an elongated oval shaped surface for receiving a prosthesis, by inserting a reamer the openings sequentially.

EP-A-661023 discloses a cutting guide which allows resection of the bone with a standard oscillating saw blade, the cutting guide having a plurality of slots such that all the cuts required can be made without re-positioning of the guide.

The techniques disclosed in these documents rely on the use of standard instruments together with an additional guide which is fixed to the bone to be resected. This means that the surgical procedure is lengthened by an initial step of fixing the guide to the bone. Furthermore, the possible shapes are limited to the particular guides used which means that, on occasions, more bone may be resected than is necessary. In addition, use of the known devices can require realignment of the milling instrument relative to the bone at various stages during the resection procedure. This is not generally compatible with the use of external alignment devices.

The present invention provides a bone resection technique in which a cutting tool such as a blade, rasp, grater or reamer rotates about a path which is defined by a tool positioning mechanism.

Accordingly, in a first aspect, the present invention provides a bone resection device for use in resection of bone during joint replacement surgery, the device comprising (a) a rotatable shaft having two cutting tools mounted on the shaft for rotation with it, each of the cutting tools being pivotally mounted on the shaft in opposed manner such that when one of the tools is caused to pivot in one direction the other tool is caused to pivot to substantially the same degree in the opposite direction, the cutting tools being arranged to cut the bone when the shaft rotates, and (b) a tool positioning mechanism mounted on the device or engaging with the device at least during use thereof and arranged to cooperate with the cutting tools during rotation thereof to alter their pivotal orientations relative to the shaft such that the shape of the resected surface is determined at least in part by the tool positioning mechanism.

Preferably, the cutting tool is arranged to slide axially along the shaft during operation of the device, for example as described below when the orientation of the cutting tool is controlled using a cam surface which is non-planar. Sliding of the tool can be achieved by mounting the pivot pin in a slot.

Preferably, each of the cutting tools is generally elongate in shape with a cutting edge towards one end and means for cooperating with the tool positioning mechanism at its opposite other end. It will generally be preferred for the cutting edge to face directly away from the end which engages the tool positioning mechanism. The shape of the cutting edge will depend on factors such as the nature of the cutting action (for example as might be performed by a blade, a rasp, a reamer or a grater), and the desired shape of the resected surface. When the resected surface has the shape of a generally rounded recess, the cutting edges will preferably be rounded.

Preferably, the cutting tools are removable from the device, and the device includes at least one other interchangeable cutting tool. This can enable the device to be used to create bone resection surfaces with desired configurations by selection of an appropriate cutting tool. Examples of tools which can be incorporated into the device include blades, reamers, graters and rasps. The device can include any of the tools of these general kinds. It can include more than one blade (or other tool), the blades (or other tools) differing from one another in terms of the configuration of the resected surface they define, for example by virtue of having different shapes or sizes.

Preferably, the tool positioning mechanism comprises a cam surface and the cooperating means comprises a cam follower such that during rotation of the cutting tool, the cam follower moves over the cam surface to control the cutting tool as it performs the resection. Preferably, the cam surface is positioned on the device and is fixed against rotation when the device is in operation, and the cam follower is provided on the cutting tool so that it rotates with the tool. It can be appropriate for the cam surface to be defined by a track or channel in which the cam follower is constrained by side walls.

Preferably, the tool positioning mechanism is removable, and the device includes at least one other interchangeable tool positioning mechanism which can be used to create resected surfaces with other configurations. For example, when the tool positioning mechanism comprises a cam surface and a cam follower, a different tool positioning mechanism can provide a different cam surface so that, when the cam follower follows that surface, the orientation of the cutting tool is controlled in a different way so as to create a different resected bone surface. The configuration of the cam surface can be selected to control the resection surface in a number of ways. It will usually be generally rounded. For many applications, it will be appropriate for the surface to be circular. However, variations in the configuration of the resected bone surface might be achieved by, for example, changing the diameter of the circular path that the cam followers follow, or by deviating from a circular for example to an oval or generally elliptical path. The cam surface will often be in a single plane. However, it will be appropriate for some applications for the path to be non-planar. This will often require that the cutting tools be arranged to slide along the axis of the device, and preferably to be biassed so that the cam follower is urged against the cam surface.

It will generally be preferred for the cam surface to have a symmetrical configuration about the axis of rotation, and for the cam surface to have as many identical portions as there are cutting tools (or a whole number multiple of the number of cutting tools).

Preferably, the cam surface is part of a cam unit which is removably engageable with the cutting tool and can either be mounted on the device or positioned relative to the bone to be resected independently of the device, and subsequently engaged with the cam follower of the cutting tool prior to use.

The tool positioning mechanism include a cam unit which can be removed from engagement with the cutting tool, and then either mounted on the device or positioned relative to the bone to be resected (for example with bone pins fixing into uncut bone) independently of the device, and subsequently engaged with the cam followers of the cutting tool prior to use. In the latter case, the cam unit may itself serve as means for providing a measured resection, with the bone pins effectively providing the point of reference for the resection.

The cam surface conveniently takes the form of a track which may be circular, triangular, oval or any other desired shape, the cam follower running around this track as the device rotates such that the cutting tools continually follow a corresponding profile to generate the desired resection surface. Examples of possible resection surfaces include flat surfaces, convex or concave spherical surfaces or conical surfaces. The configuration of the resection surface can include portions which individually are circular, triangular, oval or another shape, to provide resection surfaces which have different portions with different shapes.

The device is preferably aligned to the bone using either a central or offset locating pin, which may additionally be used as a depth stop to limit the depth of resection. Typically such a locating pin would be cylindrical, but could be of any other shape. Alternatively, other locating means could be used, particularly to position the device to other instruments, examples of such alternative locating means including a peg, boss or bearing arrangement.

Preferably, the device includes a guard which fits around the cam unit and each cutting tool, including especially the cutting edge of each tool, so as to prevent undesirable contact with soft tissue. The guard can also be used to control the extent of the resection. For example, the guard can include spikes or other locating means by which it can engage the bone in the region surrounding the surface that is to be resected to provide a point of reference against which the depth of the resection can be controlled. It can be preferred for the guard to be trimmed to fit the particular contours of the bone to be resected.

The device can include location means for controlling its location during use relative to the patient's tissue. The location means can rely on reference points provided on the patient's tissue or on the operating table.

The device can be powered or hand-operated, or both. The device can include a handle which can be arranged in line with the shaft or at an angle thereto.

In a second aspect, the invention provides a method of resecting a bone surface during joint replacement surgery, which comprises the steps of:

(a) locating on the bone surface to be resected a device which comprises (a) a rotatable shaft having two cutting tools mounted on the shaft for rotation with it, each of the cutting tools being pivotally mounted on the shaft in opposed manner such that when one of the tools is caused to pivot in one direction the other tool is caused to pivot to substantially the same degree in the opposite direction, the cutting tools being arranged to cut the bone when the shaft rotates, and (b) a tool positioning mechanism mounted on the device or engaging with the device at least during use thereof and arranged to cooperate with the cutting tools during rotation thereof to alter their pivotal orientations relative to the shaft such that the shape of the resected surface is determined at least in part by the tool positioning mechanism, and (b) rotating the shaft of the device such that the shape of the resected surface is determined at least in part by the tool positioning mechanism.

In a third aspect, the present invention provides a kit comprising a bone resection device for use in resection of bone during joint replacement surgery, the device comprising a rotatable shaft having mounted thereon for rotation with the shaft at least one cutting tool, and a set of different tool positioning mechanisms, a selected one of which is mounted on the device or engages with the device at least during use thereof and is arranged to cooperate with: the tool during rotation thereof to alter its orientation relative to the shaft such that the shape of the resected surface is determined at least in part by the particular tool positioning mechanism selected.

Preferably, the kit includes a plurality of interchangable cutting tools.

The device of the invention can be used to prepare a patient's bone to receive a component of a prosthetic joint. Examples of bones which can be prepared in this way include the tibia during implantation of a knee joint, and the glenoid during implantation of a shoulder joint.

Embodiments of the present invention will now be described, by way of example only, with reference to the accompanying drawings, in which:

FIG. 1 is a sectional view through the device of the present invention,

FIG. 2 is a side view of the device,

Figure 3:
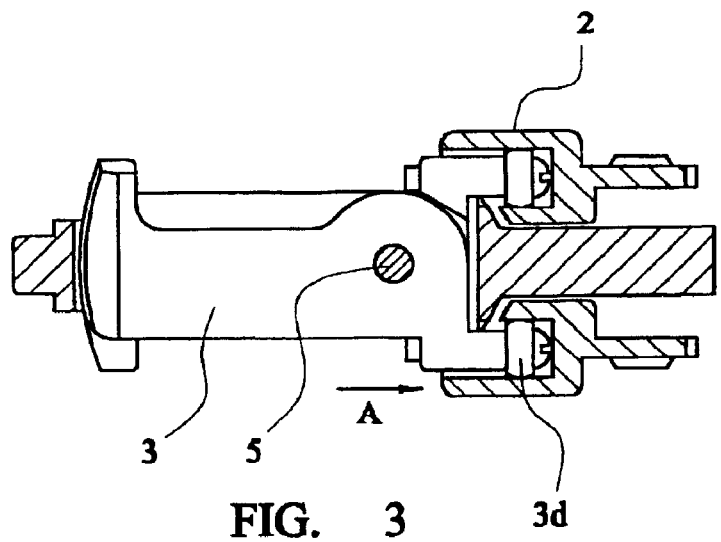
FIG. 3 is a sectional view through the cutting head of the device.
Figure 3A:
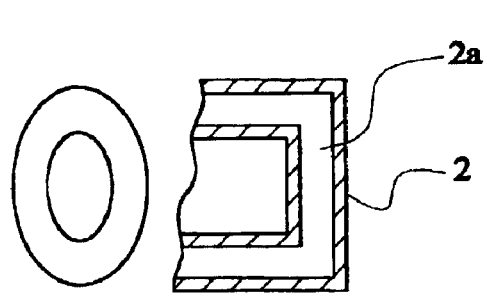
Figure 3B:
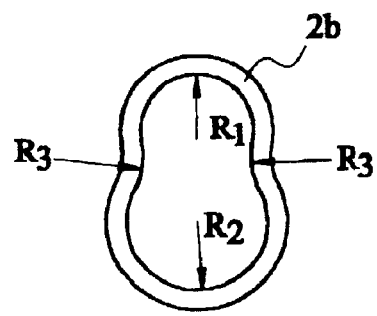
Figure 3C:
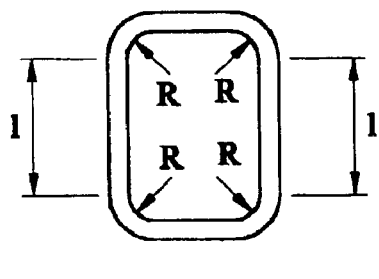
Figure 3D:
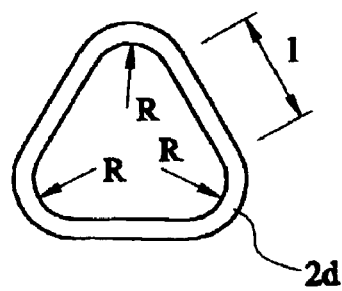
Figure 4:
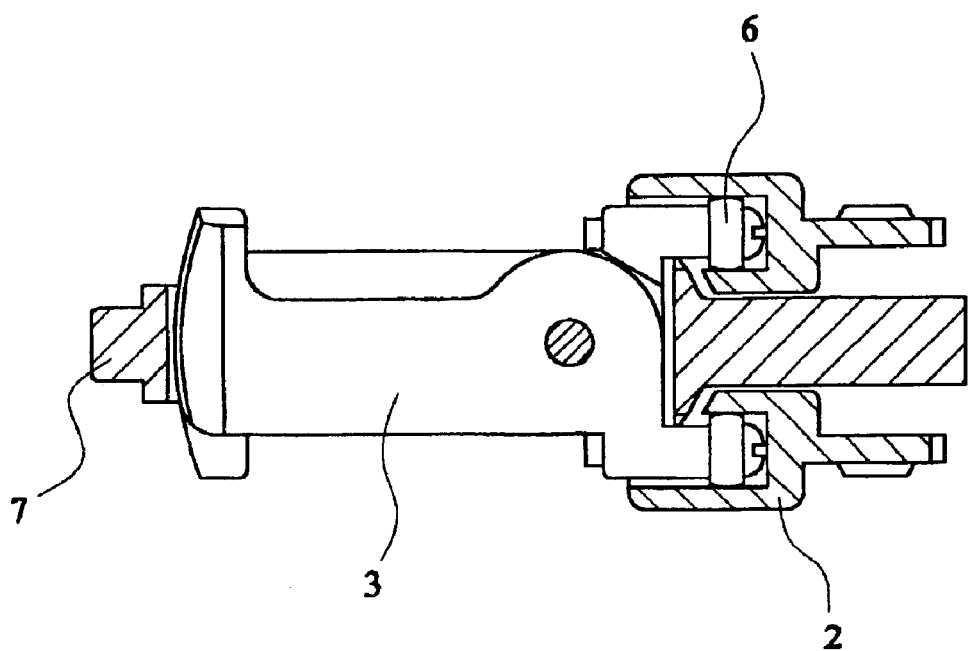
Figure 5:
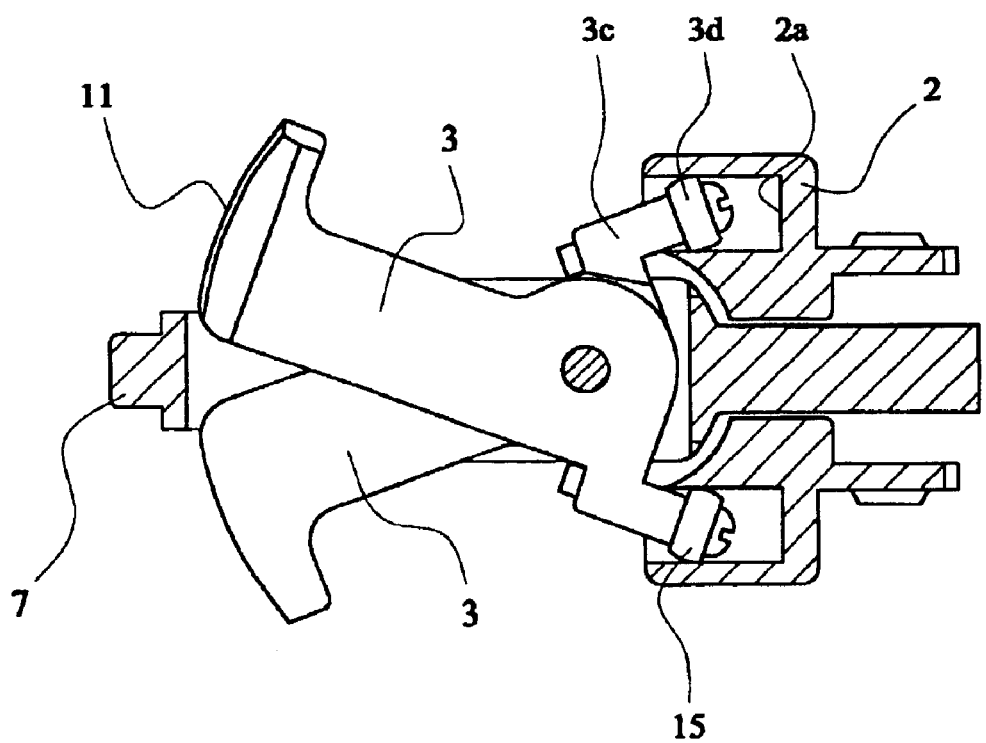
Figure 6:
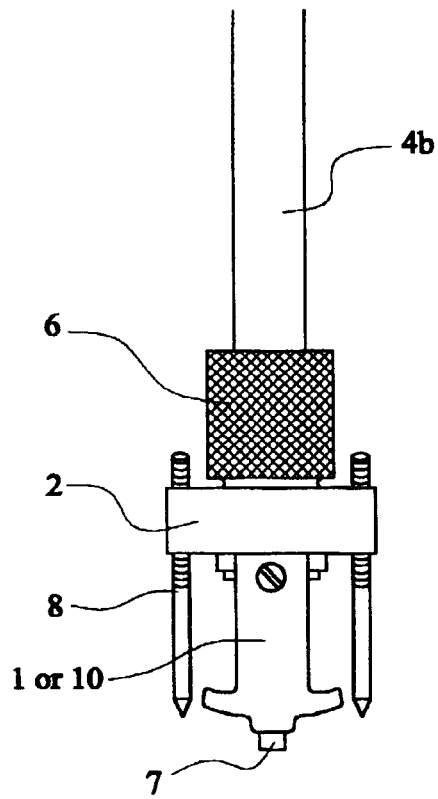
Figure 7:
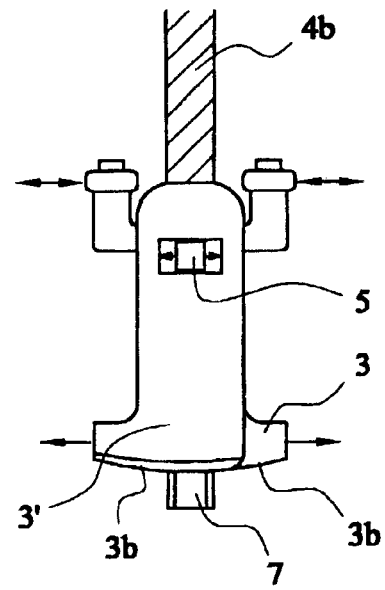
Figure 8:
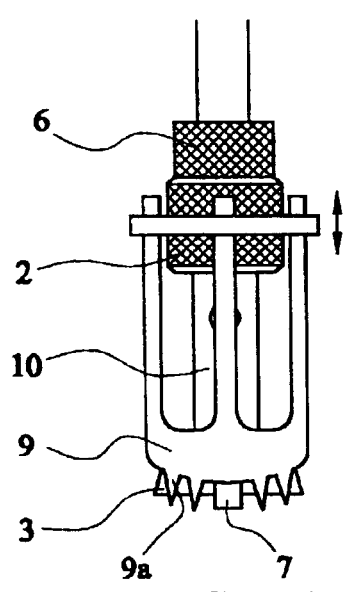
Figure 7A:
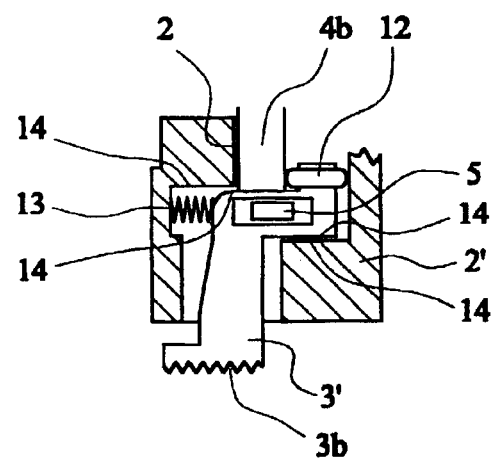

FIGS. 3A, 3B, 3C, and 3D are views of examples of different shapes of cam unit,

FIGS. 4 and 5 are side views, partially in section, of cutting blades set at minor and major axes respectively, FIG. 6 is a side view of the device of the invention, with bone pins by which it can be fixed to a patient's bone, FIG. 7 illustrates the device for use in the generation of flat cuts, FIG. 7A illustrates in detailed, sectional view the cam unit and blade arrangement of the device in FIG. 7, and FIG. 8 illustrates the soft tissue guard.

FIGS. 9A and 9B are plan and side elevation views of a cam unit, the section in FIG. 9B being taken on the line A—A in FIG. 9.

FIG. 10 is a side view of the device of the invention incorporating the cam unit shown in FIG. 9.

Referring to the drawings, FIGS. 1 and 2 show a bone resection device 30 which comprises a shaft 4 having a free end 4a which is to be connected to manual or powered drive means. The shaft is mounted for rotation within a housing 4b. A handle 32 extends generally perpendicularly to the long axis of the shaft and is secured therein by means of retainer and spring arrangement 32a.

A cam retaining device 6 is mounted on the shaft housing at the opposite end of the shaft, which retains a cam unit 2 having a cam follower track 2a defined therein. A pair of blades 3 having cutting edges 3a are pivotally mounted on a pivot pin 5 in a blade housing 10 which is in turn connected to shaft 4 for rotation therewith. Alternatively the blades 3 can be connected directly to the shaft.

A locating pin 7 (which may also be used as a depth stop) protrudes from the end of the shaft and is used to locate the device on the bone to be resected. The opposite ends of the blades 3 are formed into cam followers 3c on which are mounted retainers/bearing surfaces 3d, such that rotation of the blades will cause the cam follower surfaces 3d to follow the contours of the track 2a in the cam unit 2, around the track and also up and down within it FIGS. 3, 3A, 3B, 3C and 3D show a number of different cam units 2, each with a particular shape of track 2a which matches the required implant shape at the cutting edges 3a, for example square (2a and 2c), triangle (2d) or complex (2b).

FIG. 4 the blades 3 are shown in the narrowest position with the cam followers 3*d* are fully received within track 2*a* of cam unit 2 and lying generally in-line with the walls of the track. FIG. 5 shows the blades are in the widest position, in which the cam followers 3*d* have moved along the walls of the track and are generally at an angle thereto. It should be remembered that at the same time the cam followers 3*d* are moving around the track 2*a*.

FIG. 6 shows bone pins 8 on the cam unit 2, which can be used to control the depth of the resection relative to the surface of the surrounding bone tissue.

FIGS. 7 and 7A show a variant of the device for use in flat cuts—this uses alternative blades 3' with flat cutting edges 3*b* which are fixed to the shaft 4*b*, and an adapted cam and cam follower arrangement in which the rotational movement of the shaft is converted into linear motion of blades 3'. The blades 3' are retained within cam unit 2' and cam followers 12 comprise either a wheel or a ball to reduce friction during movement of blades 2' within cam unit 2'. A spring 13 can be used to ease movement, and a square slider 5 (which may alternatively be a wheel) is operated to generate linear motion. Alternatively or additionally, edges 14 of blades 3' may be used as cam followers against the corresponding cam surface of cam unit 2', to generate the pivoting action. This feature can also be applied to the rounded cutting blades of the previous Figures.

In FIG. 8, a guard 9, which may be trimmed to the contours of the bone, has teeth 9*a* for locating into the bone, prevents impingement of soft tissue into the cutting area. The blades 3 rotate relative to the guard and the whole device moves up and down relative to the guard as indicated by the arrow, thus also acting as a depth stop.

In use, the surgeon selects the appropriate blades and cam unit from a selection provided, according to the size and shape of the resected surface to be formed. Rotation of the blades within the cam then generates the pre-selected size and shape of resection, the depth being limited by the locating pin/depth stop 7 and/or the soft tissue guard 9.

FIGS. 9A and 9B are plan and sectional elevations through a cam unit 102 which presents a non-planar cam surface 104. While the cam surface is generally oval when viewed in plan as in FIG. 9A, the non-planarity can be seen in the side elevation of FIG. 9B.

FIG. 10 shows the device of the invention using the non-planar cam surface 104 shown in FIGS. 9A and 9B. The cutting blades 3 are mounted pivotally using a pivot pin 5, which is able to slide axially in a slot 106 in the blades. A spring 115 urges; the cutting blades, with their cam followers 3*c*, along the axis of the device, so that the pin 5 slides in the slot 106, and the cam followers are forced into the cam unit 102.

What is claimed is:

1. A bone resection device for use in resection of bone during joint replacement surgery, the device comprising (a) a rotatable shaft having two cutting tools mounted on the shaft for rotation with it, each of the cutting tools being pivotally mounted on the shaft in opposed manner such that when one of the tool is caused to pivot in one direction the other tool is caused to pivot to substantially the same degree in the opposite direction, the cutting tools being arranged to cut the bone when the shaft rotates, and (b) a tool positioning mechanism mounted on the device or engaging with the device at least during use thereof and arranged to cooperate with cutting tools during rotation thereof to alter their pivotal orientations relative to the shaft such that the shape of the resected surface is determined at least in part by the tool positioning mechanism, in which:

(i) the cutting edge of each of the cutting tools faces directly away from the tool positioning mechanism, and (ii) the tool positioning mechanism comprises a cam surface and cam follower assembly which controls the pivotal position of the cutting tools according to the movement of the cam follower over the cam surface during rotation of the shaft, the cam surface defining a path for the cam followers which is shaped so that the cutting tools move pivotally during rotation of the shaft to cause the shape of the bone surface that is resected by the cutting tools to be non-circular when the resected bone is viewed along the axis defined by the shaft.

2. A bone resection device as claimed in claim 1, in which each of the cutting tools is generally elongated in shape with a cutting edge towards one end and means for cooperating with the tool positioning mechanism at its opposite other end.

3. A bone resection device as claimed in claim 1, in which the cutting tools are removable and the device includes at least one other interchangeable cutting tool.

4. A bone resection device as claimed in claim 1, in which the tool positioning mechanism is removable, and the device includes at least one other interchangeable tool positioning mechanism which defines other configurations of resection surfaces.

5. A bone resection device as claimed in claim 1, in which the cam surface is part of a cam unit which is removably engageable with the cutting tools and can either be mounted on the device or positioned relative to the bone to be resected independently of the device, and subsequently engaged with the cam followers of the cutting tools prior to use.

6. A bone resection device as claimed in claim 5, in which the cam surface is in the form of a track which the cam followers can follow as the device rotates such that the cutting tools follow a corresponding profile to generate the desired resection surface.

7. A bone resection device as claimed in claim 1, which includes a locating pin to define the axis on which the device rotates.

8. A bone resection device as claimed in claim 1, which includes a guard which fits around the cutting tool and the tool positioning mechanism.

9. A bone resection device as claimed in claim 2, in which the cutting tools are removable and the device includes at least one other interchangeable cutting tool.

10. A bone resection device as claimed in claim 2, in which the tool positioning mechanism is removable, and the device includes at least one other interchangeable tool positioning mechanism which defines other configurations of resection surfaces.

11. A bone resection device as claimed in claim 2, in which the cam surface is part of a cam unit which is removably engageable with the cutting tools and can either be mounted on the device or positioned relative to the bone to be resected independently of the device, and subsequently engaged with the cam followers of the cutting tools prior to use.

12. A bone resection device as claimed in claim 2, which includes a locating pin to define the axis on which the device rotates.

13. A bone resection device as claimed in claim 2, which includes a guard which fits around the cutting tool and the tool positioning mechanism.

14. A bone resection device as claimed in claim 3, in which the tool positioning mechanism is removable, and the device includes at least one other interchangeable tool positioning mechanism which defines other configurations of resection surfaces.

15. A bone resection device as claimed in claim 3, in which the cam surface is part of a cam unit which is removably engageable with the cutting tools and can either be mounted on the device or positioned relative to the bone to be resected independently of the device, and subsequently engaged with the cam followers of the cutting tools prior to use.

16. A bone resection device as claimed in claim 3, which includes a locating pin to define the axis on which the device rotates.

17. A bone resection device as claimed in claim 3, which includes a guard which fits around the cutting tool and the tool positioning mechanism.

18. A method of resecting a bone surface during joint replacement surgery, which comprises the steps of:

(a) locating on the bone surface to be resected a bone resection device for use in resection of bone during joint replacement surgery, the device comprising (a) a rotatable shaft having two cutting tools mounted on the shaft for rotation with it, each of the cutting tools being pivotally mounted on the shaft in opposed manner such that when one of the tools is caused to pivot in one direction the other tool is caused to pivot to substantially the same degree in the opposite direction, the cutting tools being arranged to cut the bone when the shaft rotates, and (b) a tool positioning mechanism mounted on the device or engaging with the device at least during use thereof and arranged to cooperate with the cutting tools during rotation thereof to alter their pivotal orientations relative to the shaft such that the shape of the resected surface is determined at least in part by the tool positioning mechanism, in which (i) the cutting edge of each of the cutting tools faces directly away from the tool positioning mechanism, and (ii) the tool positioning mechanism comprises a cam surface and cam follower assembly which during rotation of the shaft, controls the pivotal position of the cutting tools according to the movement of the cam follower over the cam surface, the cam surface defining a non-circular path for the cam followers so that the surface that is resected by the cutting tools has a non-circular shape, and (b) rotating the shaft of the device such that the shape of the resected surface is determined at least in part by the tool positioning mechanism.

19. A kit comprising a bone resection device for use in resection of bone during joint replacement surgery, the device comprising (a) a rotatable shaft having two cutting tools mounted on the shaft for rotation with it, each of the cutting tools being pivotally mounted on the shaft in opposed manner such that when one of the tools is caused to pivot in one direction the other tool is caused to pivot substantially the same degree in the opposite direction, the cutting tools being arranged to cut the bone when the shaft rotates, and (b) a set of different tool positioning mechanisms, a selected one of which is mounted on the device or engaging with the device at least during use thereof and arranged to cooperate with the cutting tools during rotation thereof to alter their pivotal orientations relative to the shaft such that the shape of the resected surface is determined at least in part by the tool positioning mechanism, in which (i) the cutting edge of each of the cutting tools faces directly away from the tool positioning mechanism, and (ii) the tool positioning mechanism comprises a cam surface and cam follower assembly which during rotation of the shaft, controls the pivotal position of the cutting tools according to the movement of the cam follower over the cam surface, the cam surface defining a non-circular path for the cam follower so that the surface that is resected by the cutting tools has a non-circular shape.

20. A kit as claimed in claim 19, which includes a set of cutting tools having differently shaped cutting edges.

* * * * *